United States Patent
Purdy

(10) Patent No.: US 12,310,704 B2
(45) Date of Patent: May 27, 2025

(54) BLOOD PRESSURE MONITORING WITH ZERO FUNCTION SYSTEM AND METHOD

(71) Applicant: ENDOPHYS HOLDINGS, LLC, Dallas, TX (US)

(72) Inventor: Phillip D. Purdy, Maypearl, TX (US)

(73) Assignee: Endophys Holdings, LLC, Dallas, TX (US)

(*) Notice: Subject to any disclaimer, the term of this patent is extended or adjusted under 35 U.S.C. 154(b) by 52 days.

(21) Appl. No.: 18/202,388

(22) Filed: May 26, 2023

(65) Prior Publication Data
US 2023/0301528 A1    Sep. 28, 2023

Related U.S. Application Data

(63) Continuation of application No. 16/825,712, filed on Mar. 20, 2020, now Pat. No. 11,666,233.
(Continued)

(51) Int. Cl.
*A61B 5/0215* (2006.01)
*A61B 5/00* (2006.01)
(Continued)

(52) U.S. Cl.
CPC ...... *A61B 5/02156* (2013.01); *A61B 5/02152* (2013.01); *A61B 5/032* (2013.01);
(Continued)

(58) Field of Classification Search
CPC ............ A61B 5/02156; A61B 5/02152; A61B 5/0215; A61B 5/021; A61B 5/02;
(Continued)

(56) References Cited

U.S. PATENT DOCUMENTS

| | | | |
|---|---|---|---|
| 3,894,535 A | * | 7/1975 | Cannon ............... A61B 5/021 600/485 |
| 4,342,218 A | * | 8/1982 | Fox ................. A61B 5/02156 73/1.62 |

(Continued)

FOREIGN PATENT DOCUMENTS

| | | |
|---|---|---|
| EP | 2299574 A2 | 3/2011 |
| EP | 4027884 A1 | 7/2022 |

(Continued)

OTHER PUBLICATIONS

Fiber Optic Measurement System/Fiber Optic Blood Pressure Sensors Instruction Manual, World Precision Instruments, Inc. 2004 (Year: 2004).

(Continued)

*Primary Examiner* — Mohamed Charioui
(74) *Attorney, Agent, or Firm* — James H Ortega; David W. Carstens; Carstens, Allen & Gourley, LLP

(57) ABSTRACT

A system and method for monitoring the blood pressure of a patient that allows for a device sensor to be recalibrated according to atmospheric pressure without removing the device sensor from inside the patient. This permits quickly monitoring the blood pressure of a patient if a re-zero is needed. The invention has a blood pressure monitor (BPM) that obtains an atmospheric pressure observation. The atmospheric pressure observation is adjusted and stored to memory as a zero value. The zero value is retrieved to recalibrate the system and method if a device sensor has been disconnected from and reconnected to the same or a different BPM, the patient has been moved such that the surroundings have been altered to make it necessary to recalibrate according to atmospheric pressure, and/or the device sensor has been connected to a different patient care monitor.

20 Claims, 7 Drawing Sheets

Related U.S. Application Data

(60) Provisional application No. 62/900,256, filed on Sep. 13, 2019.

(51) Int. Cl.
*A61B 5/03* (2006.01)
*A61B 5/20* (2006.01)

(52) U.S. Cl.
CPC ............ *A61B 5/205* (2013.01); *A61B 5/6848* (2013.01); *A61B 5/6851* (2013.01); *A61B 5/6852* (2013.01); *A61B 2560/0223* (2013.01); *A61B 2560/0257* (2013.01); *A61B 2560/0475* (2013.01); *A61B 2562/0247* (2013.01)

(58) Field of Classification Search
CPC .. A61B 5/00; A61B 5/032; A61B 5/03; A61B 5/205; A61B 5/202; A61B 5/20; A61B 5/6848; A61B 5/6851; A61B 5/6852; A61B 5/68; A61B 2560/0223; A61B 2560/0257; A61B 2560/0475; A61B 2562/0247; A61B 2562/0242; A61B 2562/02
See application file for complete search history.

(56) References Cited

U.S. PATENT DOCUMENTS

| | | |
|---|---|---|
| 4,446,715 A | 5/1984 | Bailey |
| D285,112 S | 8/1986 | Sato et al. |
| 4,648,406 A | 3/1987 | Miller |
| 4,691,708 A | 9/1987 | Kane |
| 4,703,757 A | 11/1987 | Cohen |
| 4,705,047 A | 11/1987 | Bailey |
| 4,711,246 A | 12/1987 | Alderson |
| 4,778,987 A | 10/1988 | Saaski et al. |
| 4,787,396 A | 11/1988 | Pidorenko |
| 4,858,615 A | 8/1989 | Meinema |
| 4,901,735 A | 2/1990 | Berg |
| 5,048,524 A | 9/1991 | Bailey |
| 5,103,832 A | 4/1992 | Jackson |
| 5,107,847 A | 4/1992 | Knute et al. |
| D329,702 S | 9/1992 | Sato et al. |
| 5,325,865 A | 7/1994 | Beckman et al. |
| 5,482,049 A | 1/1996 | Addiss et al. |
| 5,485,741 A | 1/1996 | Madison |
| 5,566,680 A | 10/1996 | Urion et al. |
| 5,568,815 A | 10/1996 | Raynes et al. |
| D375,792 S | 11/1996 | Hillman et al. |
| 5,668,320 A | 9/1997 | Cowan |
| 5,691,478 A | 11/1997 | Barry et al. |
| D414,870 S | 10/1999 | Saltzstein et al. |
| 5,987,995 A | 11/1999 | Sawatari et al. |
| 6,120,457 A | 9/2000 | Coombes et al. |
| 6,210,346 B1 | 4/2001 | Hall et al. |
| 6,231,524 B1 | 5/2001 | Wallace et al. |
| 6,409,677 B1 | 6/2002 | Tulkki |
| 6,471,646 B1 | 10/2002 | Thede |
| 6,585,660 B2 | 7/2003 | Dorando et al. |
| 7,144,372 B2 | 12/2006 | Ng et al. |
| D547,454 S | 7/2007 | Hsieh |
| D558,351 S | 12/2007 | Diener et al. |
| 7,318,807 B2 | 1/2008 | Ng |
| 7,335,162 B2 | 2/2008 | Eide |
| 7,361,147 B2 | 4/2008 | Ng |
| 7,503,897 B2 | 3/2009 | Ng et al. |
| D590,509 S | 4/2009 | Costa |
| D598,113 S | 8/2009 | Flaction et al. |
| D606,659 S | 12/2009 | Kiani et al. |
| D608,452 S | 1/2010 | Huang |
| 7,724,148 B2 | 5/2010 | Samuelsson et al. |
| D618,355 S | 6/2010 | Delaey |
| D621,515 S | 8/2010 | Chua et al. |
| 7,946,997 B2 | 5/2011 | Hubinette et al. |
| 8,016,763 B2 | 9/2011 | Eide |
| 8,066,681 B1 | 11/2011 | Hall et al. |
| D650,484 S | 12/2011 | Shinohara et al. |
| D652,522 S | 1/2012 | Koester |
| 8,133,184 B2 | 3/2012 | Williams et al. |
| D659,836 S | 5/2012 | Bensch et al. |
| 9,931,043 B2 | 4/2018 | Wilson et al. |
| 2003/0045781 A1 | 3/2003 | Rosenheimer |
| 2004/0082866 A1 | 4/2004 | Mott et al. |
| 2004/0147847 A1 | 7/2004 | Ng et al. |
| 2006/0272383 A1 | 12/2006 | Huang et al. |
| 2007/0088223 A1 | 4/2007 | Mann et al. |
| 2007/0106165 A1 | 5/2007 | Tulkki |
| 2007/0112274 A1 | 5/2007 | Heitzmann et al. |
| 2007/0112277 A1 | 5/2007 | Fischer et al. |
| 2007/0287924 A1 | 12/2007 | Glocker et al. |
| 2008/0100440 A1 | 5/2008 | Downie et al. |
| 2008/0119758 A1 | 5/2008 | Samuelsson et al. |
| 2008/0159738 A1 | 7/2008 | Lavranchuk |
| 2008/0250341 A1 | 10/2008 | Dlugos et al. |
| 2008/0269573 A1 | 10/2008 | Najafi et al. |
| 2010/0052863 A1 | 3/2010 | Renfro, Jr. et al. |
| 2010/0234698 A1 | 9/2010 | Manstrom et al. |
| 2010/0244813 A1 | 9/2010 | Hynd et al. |
| 2010/0286536 A1 | 11/2010 | Samuelsson et al. |
| 2011/0046477 A1 | 2/2011 | Hulvershorn et al. |
| 2011/0071407 A1 | 3/2011 | Hübinette et al. |
| 2012/0041334 A1 | 2/2012 | Goedje et al. |
| 2012/0071744 A1 | 3/2012 | Euliano et al. |
| 2012/0123223 A1 | 5/2012 | Freeman et al. |
| 2012/0179012 A1 | 7/2012 | Saffarian |
| 2012/0238869 A1 | 9/2012 | Schmitt et al. |
| 2013/0046190 A1 | 2/2013 | Davies |
| 2013/0131523 A1 | 5/2013 | Suchecki et al. |
| 2013/0225941 A1 | 8/2013 | Samuelsson et al. |
| 2014/0024956 A1* | 1/2014 | Purdy ................ A61B 5/02156 73/753 |
| 2014/0180140 A1 | 6/2014 | Alpert |
| 2015/0112211 A1 | 4/2015 | Purdy |

FOREIGN PATENT DOCUMENTS

| | | |
|---|---|---|
| WO | 9310705 A1 | 6/1993 |
| WO | 2018058227 A1 | 4/2018 |

OTHER PUBLICATIONS

Hashemian et al., "Assessment of Fiber Optic Pressure Sensors", 1995, Analysis and Measurement Services Corporation (Year: 1995).

Phillip Purdy et al., "Use of a pressure sensing sheath: comparison with standard means of blood pressure monitoring in catheterization procedures", 2017 J. Neurointervent Surg. 9:766-771.

RJC Enterprises, LLC "Supporting Instrumentation—Model 600" Fiber Optic Sensor, retrieved from www.rjcenterprises.net/model600.html, Nov. 1, 2012, 1 page.

\* cited by examiner

BLOOD PRESSURE MONITORING WITH ZERO FUNCTION SYSTEM AND METHOD

CROSS-REFERENCE TO RELATED APPLICATIONS

This application is a continuation of, and thus claims benefit under 35 U.S.C. § 120, U.S. patent application Ser. No. 16/825,712, filed on Mar. 20, 2020, now U.S. Pat. No. 11,666,233, which claims benefit to U.S. Patent Application Ser. No. 62/900,256, filed Sep. 13, 2019, both of which are incorporated herein by reference in their entireties for all purposes.

BACKGROUND

Technical Field

The present disclosure relates to measuring pressure inside a patent. More particularly, and not by way of limitation, the present disclosure is directed to a system and method for recalibrating a blood pressure sensor without having to remove the sensor from inside a patient.

Description of Related Art

In healthcare in humans and others, monitoring of "vital signs" (pulse rate, respirations, blood pressure, temperature, etc.) is done routinely at different intervals. In more invasive procedures (surgical, catheter interventions, etc.), vital sign monitoring is performed at increased frequency and the accuracy of such monitoring can have a salutary effect on the outcome of the procedures.

Blood pressure monitoring may be performed using a sphygmomanometer (blood pressure cuff) inflated around an arm or a leg and auscultation is performed during deflation of the cuff to "hear" the pulsations arrive and dissipate during cuff deflation, identifying systolic and diastolic blood pressures, respectively. However, sphygmomanometer observations are performed infrequently—30 seconds or longer inter-observation interval—and are often compromised by external factors (obesity, atherosclerotic changes, air, pressure, etc.).

Therefore, in the setting of general anesthesia and more invasive procedures, more frequent and accurate samplings are desirable. In these settings, "invasive" blood pressure monitoring is often performed using a catheter placement inside an artery (most often the radial artery in the wrist) and pressures are obtained by connecting the radial artery catheter, via a fluid-filled section of tubing, to a Wheatstone Bridge transducer. The reference to the foregoing can be found in Phillip Purdy et al., *Use of a pressure sensing sheath: comparison with standard means of blood pressure monitoring in catheterization procedures*, 2017 J. NEUROINTERVENT SURG. 9:766-771 and incorporated herein by reference. The Wheatstone Bridge transducer communicates via cable with standard patient care monitors (PCM) to yield analog tracings of the waveform created within the artery to yield systolic, diastolic, and mean arterial pressures. There is an issue related to the Wheatstone Bridge transducer technology, described in the cited article yielding various degrees of error and potential complications related to placement of the separate radial artery catheter.

Often, in urgent medical settings (stroke, heart attack, hemorrhage, etc.), catheter-based procedures can be performed to treat or otherwise intervene. These procedures most often involve placement of a type of medical device such as a catheter, needle, guidewire, or a sheath in the artery at the beginning of the procedure and sensors used for the intervention can be placed via that medical device and advanced to the ultimate target organ (brain, heart, etc.). The term "medical device" is defined to include a device that functions, inter alia, to measure a pressure within a blood vessel (artery or vein), bladder, cerebrospinal fluid structure, or other organ in which pressure measurement is desirable, which contains a Fabry-Perot sensor for achieving that pressure measurement. Due to the urgency of these problems, delays related to placement of the separate radial artery catheter (delays of 10-30 minutes or longer) may be undesirable.

In response to this issue, a medical device was developed that incorporates a different type of pressure sensing technology (fiberoptic Fabry-Perot sensor) into the wall of the medical device and digital arterial pressure measurements can be obtained at frequencies of hundreds of observations per second with resolutions of 0.1-0.2 mmHG. This resulted in issuance of patents in the U.S. and elsewhere on both the medical device and the Blood Pressure Monitor device to which it is connected.

The Blood Pressure Monitor is connected in many settings to a standard patient care monitor via the patient monitor interface described in Transducer Interface System and method, U.S. Pat. No. 8,926,520 (filed Jun. 19, 2013) (issued Jan. 6, 2015) which is incorporated herein by reference.

The term "blood pressure" refers to the difference measured between the pressure in the atmosphere ("0" pressure) and the pressure generated via the contractions of the heart and transmitted to the arteries. These pressures are read as "systolic" pressure (i.e., the peak pressure of the cardiac cycle) and "diastolic" pressure (the trough pressure of the cardiac cycle). All patient care monitors measure blood pressure by first identifying for the monitor what is the atmospheric pressure. This atmospheric pressure is read as "0" by the patient care monitor and must be input in the beginning of the procedure before the monitor can identify how much higher than atmospheric pressure the pressure in the arteries achieves. All patient care monitors have a "zero" button or switch which, when depressed or otherwise activated, records, in the monitor the observed level of pressure in the atmosphere. Performance of a zero calibration is a mandatory function for invasive blood pressure monitoring on patient care monitors.

The use of a Wheatstone Bridge transducer involves the following steps:
 a. Placement of the artery catheter as described above.
 b. Connection of the artery catheter, via fluid-filled tubing, to the Wheatstone Bridge transducer, which has been suspended on a standard IV pole at the approximate level of the patient's heart (one source of error).
 c. A "3-way" stopcock is connected between the fluid-filled tubing and the Wheatstone Bridge.
 d. The stopcock includes a selector valve between 2 inputs and there is one other "way" on the stopcock constituting the output.
 e. One input of the stopcock ("A") connects to the tubing and the other input has no connection (i.e., the arm of the stock opens to room air-"B")).
 f. The output of the stopcock connects to the Wheatstone Bridge ("C"). Hence, when the stopcock is open to air, the Wheatstone Bridge "sees" air pressure.
 g. When the stopcock is open to the artery catheter, the Wheatstone Bridge "sees" blood vessel pressure.

"Zeroing" the Wheatstone Bridge to the patient care monitor as follows:
  a. The stopcock has been initially connected to A.
  b. The stopcock is temporarily closed to A and opened to B.
  c. While the stopcock is opened to B, the "zero" button on the patient care monitor is depressed and held depressed until the monitor displays "0".
  d. The monitor is now "zeroed" to room air, and the stopcock is switched back to its B arm communication with the Wheatstone Bridge. The pressures "seen" by the monitor now are the pressures in the artery, and the pressures displayed are the high (systolic) and low (diastolic) pressures in comparison to be remembered "zero" pressure. These pressures are displayed as mmHg (millimeters of mercury).

Since all pressures obtained from the Fabry-Perot sensor ("sensor") in the medical device are obtained from the diaphragm of the sensor, which will be inside the artery as soon as the sheath medical device is inserted, the sensor must be "zeroed" prior to insertion in the artery. This is currently done via connection of the sensor output to the blood pressure monitor (BPM) prior to sensor insertion into the artery, and the Zero value is obtained within the blood pressure monitor and while the sensor is not in the artery, the "Zero" button on the patient care monitor is depressed, per step c above. The zero-calibration value from the sensor can then be stored in the BPM, and if, for some reason, the sensor (medical device) is disconnected from the BPM, upon reconnection to the BPM the BPM identifies the sensor and collects the zero calibration from its memory. When the PCM has not been "re-zeroed" or disconnected from the BPM during the interruption, the remembered zero allows the blood pressure monitor to communicate pressures accurately to the patient care monitor. A failure to properly "zero" and account for atmospheric pressure will lead to incorrect pressure measurements and possibly incorrect medical care as a result.

Deficiencies in the Prior Art

There are circumstances in medical care where this zeroing methodology may be disadvantageous: (1) The patient care monitor may malfunction, (2) requiring its replacement with another patient care monitor, and (3) the new patient care monitor has not been "zeroed" before, and the sensor cannot be zeroed to the BPM without removing the medical device from the artery.

A need exists for an improved method of "zeroing" the blood pressure monitor/medical device combination to the patient care monitor that allow the Fabry-Perot sensors to remain in the artery throughout the procedure. Thus, there is a need to save the "zero" from the sensor in the event that there is a technical interruption of signal to the patient care monitor during a procedure or in the event that there is a reason for the patient to be changed from one patient care monitor to another, or even from one blood pressure monitor to another.

The patient may be transported from one location to another, and it may be medically desirable to continue monitoring his/her blood pressure. Since it is often infeasible to move the monitor with the patient (e.g. there are fixed-placement monitors in catheterization labs and fixed-placement monitors in recovery rooms, intensive care units, or routine hospital rooms) and infeasible to re-zero the medical device to the new monitor without removing the medical device (sensor) from the artery, a means to save the zero calibration from the time of the initial "zero calculation" and transfer it to a new patient care monitor or retransmit it to the same monitor (for example, after a power supply interruption) is needed.

There may be blood pressure monitoring devices that remain with the care delivery location when that patient is transferred to a subsequent different monitor. Therefore, what is needed is the development a mechanism to "re-zero" a patient care monitor to a sensor after the sensor is placed in an artery. This submission proposes alternative solutions to the zeroing problem that addresses some or all of these shortcomings.

Finally, any sensor used in the system may have a correction factor, sometime referred to as a gauge value. This is an amount that the sensor is consistently off in its measurements. While the suppliers of sensors attempt to keep this number de minimis, its value should still be understood as a source of error that should be stored and used to correct any measured reading.

Objective of the Invention

The objectives identified below should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above. Accordingly, the objectives of the present invention are (among others) to circumvent the deficiencies in the prior art and affect the following objectives: provide for a system and method that allows for a sensor inserted into a patient to be "re-zeroed" without removing the sensor from the patient.

BRIEF SUMMARY

The present invention is directed to a system and method for adjusting a pressure reading in accordance with atmospheric pressure when a medical device sensor has been already inserted inside a patient and when removing the sensor from the patient to get a new atmospheric pressure observation is not advantageous or ideal. When the medical device sensor has already been inserted into the patient, the medical device is then coupled to a standard blood pressure monitor. The blood pressure monitor obtains an atmospheric pressure. By coupling the medical device sensor to the blood pressure monitor, the blood pressure monitor is configured to execute a zero function.

This zero function is designed to produce a zero value, wherein the zero value is derived from an adjusted atmospheric pressure observation which is based on gauge factors that are specific to the medical device sensor and an atmospheric pressure observation. When a new zero value is produced, any pre-existing zero value that was already stored in the non-volatile memory is erased or modified by the new zero value which can be is stored in in the pre-existing zero value's place. The gauge factors in the preferred embodiment are stored in non-volatile memory and are communicated to the blood pressure monitor when the medical device is coupled to the blood pressure monitor. When the analog pressure sensor inside the patient takes an observation of the patient's blood pressure, the observation is utilized, along with the zero value to produce a compensated pressure value.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1:
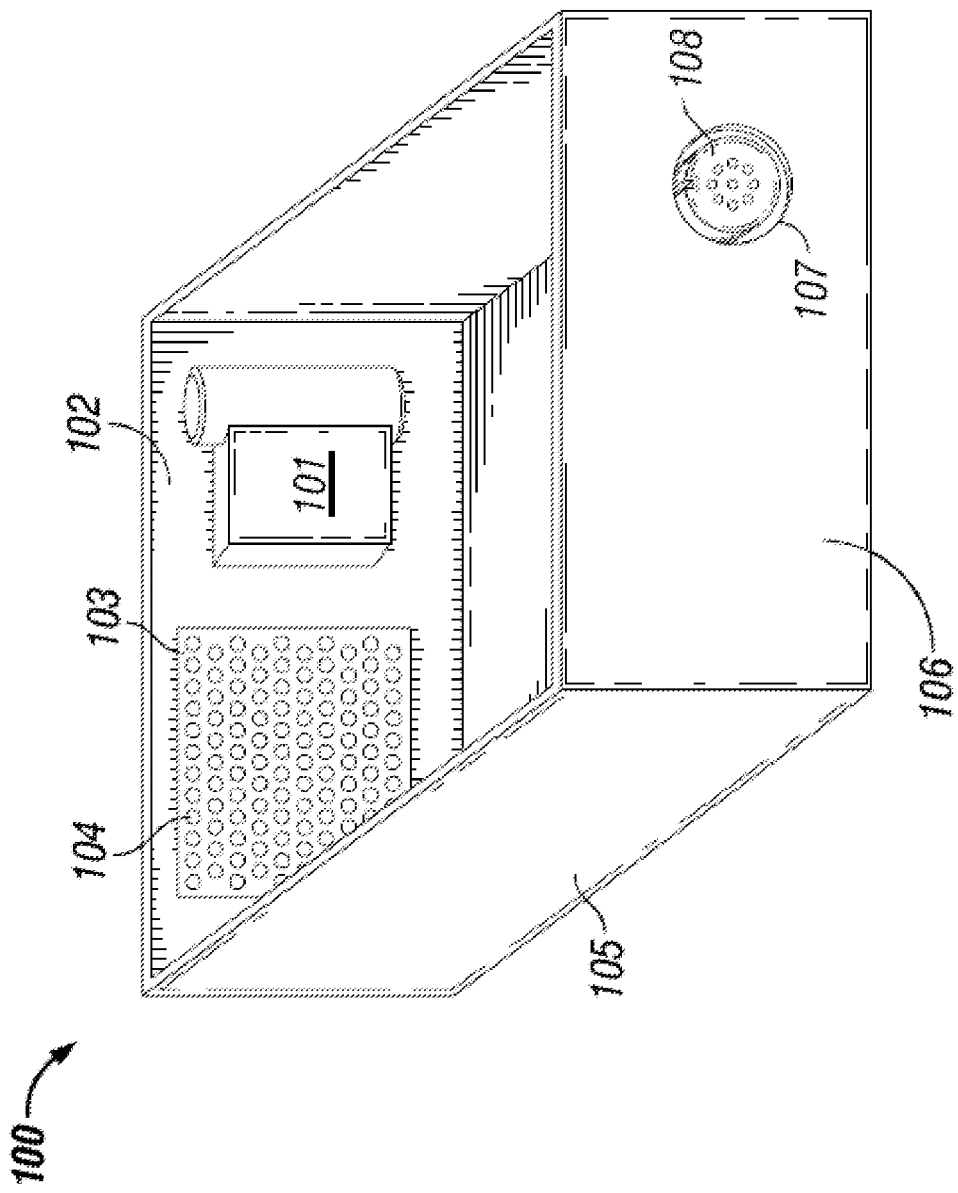
FIG. 1 is a perspective view of one embodiment of the present invention displaying a blood pressure monitor sensor that has is cover removed and is exposed to atmospheric pressure.

The present invention is directed to a system and method for performing a zero function that produces a zero value which is necessary to adjust a blood pressure observation taken by a medical device sensor inside a patient without removing the medical device sensor from the patient. Generally, the invention initiates the zero function when the medical device sensor is coupled in some manner to a pressure monitor and the monitor is configured to obtain a pressure reading with a pressure sensor that is exposed to atmospheric pressure.

Definitions

The following are several definitions used in reference to the present invention:

1. Medical device: A device (sheath, catheter, needle, guidewire or other structure), which possesses, inter alia, the function to measure a pressure within a particular part of a patient's body such as a blood vessel (artery or vein), bladder, cerebrospinal fluid structure, or other organ in which pressure measurement is desirable, which contains a Fabry-Perot sensor for achieving that pressure measurement. All subsequent references to "sheath" are intended to refer to any sheath, catheter, needle, guidewire or other structure, per this definition. For more information regarding the medical device such as a sheath and the sheath analog sensor refer to Multi-Sheath Member Apparatus, U.S. Pat. No. 8,961,452 (filed Mar. 6, 2012) (issued Feb. 24, 2015) which is incorporated herein by reference.
2. Medical device sensor: sensor contained in the medical device. The medical device sensor is unique for every device.
3. Blood Pressure Monitor (BPM): an apparatus (one or more devices) to which the medical device sensor is connected which is interposed between the medical device of (1) above and a standard patient care monitor. The pressure monitor contains the pressure sensor of (4) below and connects simultaneously to the medical device sensor and to the standard patient care monitor manufactured currently by many vendors (GE, Philips, etc.). Analog input from the medical device sensor is converted to digital output values for calculation of discrete pressures from the medical device sensor, and subsequently converted back to analog output for purposes of display of pressures on the patient care monitor.
4. Pressure Monitor Sensor: sensor that is in communication with the blood pressure monitor. This is unchanging from device to device and is used to monitor atmospheric pressure. However, the gauge factors for each sensor are different. Therefore, in order for a zero calibration of the medical device sensor to be read from the blood pressure monitor sensor, the zero value from the blood pressure monitor sensor must be calculated from the blood pressure monitor sensor gauge factors and converted to the reading that have been given based on the medical device sensor gauge factors.
5. Zero switch: an apparatus, located on the BPM, for initiating a zero-function located on the patient care monitor that does not require the medical device analog sensor to be decoupled and then recoupled with the blood pressure monitor.

One embodiment of the present invention includes connecting the sheath to a blood pressure monitor. The sheath can contain a pressure sensor such a Fabry-Perot fiber optic sensor that is inserted into the patient and maneuvered into the desired location in the patient in order to observe the pressure at that particular location. In addition, the blood pressure monitor is also coupled to a patient care monitor.

The blood pressure monitor obtains an atmospheric pressure reading. This can be done by either communicating with the patient care monitor to receive an atmospheric pressure reading from it or receiving an atmospheric pressure observation from a second blood pressure sensor that is in communication with blood pressure monitor. In the later scenario, the second blood pressure sensor can either be coupled to the blood pressure monitor or in communication with the blood pressure monitor through a wireless means. The second blood pressure monitor communicates the atmospheric pressure, along with any correction factors, to the blood pressure monitor. Then the blood pressure monitor calculates an adjusted atmospheric pressure reading from the atmospheric pressure observation and the correction factors associated with the second sensor.

Regardless of where the blood pressure monitor receives the atmospheric pressure reading from, the blood pressure monitor checks to see if the pressure readings from the blood pressure sensor are constant or variable.

If the observed readings are constant, the blood pressure monitor checks the memory storage to see if a prior zero value is recorded. If none, the blood pressure monitor records atmospheric pressure as a zero value in the memory. The memory can be a non-volatile memory such as either EPROM or EEPROM. Also, it can be located in the medical device or located in the blood pressure monitor. If there is not any zero value already recorded, then the blood pressure monitor records the observed atmospheric pressure as the zero value in the memory storage.

However, if the atmospheric pressure readings are variable, the blood pressure monitor checks the memory storage to see if it contains a prior zero value. If a zero value is present, the blood pressure monitor checks to see if that zero value matches its observed internal value of atmospheric pressure within an accepted error range. If "yes" (i.e., matched values between the value contained in the memory and the blood pressure monitor adjusted atmospheric pressure observation), no changes are made to the zero-value recorded on the memory storage. But if "no", the zero value is corrected to reflect current atmospheric pressure. This circumstance is anticipated to be uncommon, if not rare, wherein a patient is moved from one atmospheric pressure condition to another or wherein atmospheric pressure changes significantly between connections to a blood pressure monitor while the sheath sensor remains in a patient. If sheath pressure readings are variable and no prior zero value is recorded, the blood pressure monitor will display an error message—i.e., zeroing of the sensor is not feasible under current circumstances.

In one embodiment, the patient care monitor initiates a pressure reset function when the blood pressure monitor has been disconnected from a first patient care monitor and connected to a second patient care monitor. The second patient care monitor reads the zero-value from the memory storage and resets the zero value from the memory. The zero switch defined above may be used to specify transmission of the stored zero value from the blood pressure monitor to the patient care monitor.

In an alternate embodiment, the medical device has been disconnected from a blood pressure monitor and then reconnected to a either the same or a second blood pressure monitor. The blood pressure monitor that is now connected to the medical device queries to determine if there is a pre-existing stored zero value, if there is not one established then it establishes a new zero-value and stores it in memory. In another embodiment, the zero function is initiated when an interruption has occurred in the communication of the sensed signal from the device sensor and there is a need to re-zero. The zero-value is read from the memory storage and resets the zero value from the memory. Again, the zero switch may be used to specify transmission of the stored zero value from the blood pressure monitor to the patient care monitor.

Blood pressure measurement is the measurement of pressure inside arteries compared to the atmospheric pressure being applied outside of a patient. The ability to perfuse tissue via blood vessels requires a pressure inside the vessel to exceed the pressure applied from outside the patient. In the most extreme example, application of pressure outside a patient via a tourniquet arrests all circulation because the external pressure equals or exceeds internal pressure. "Zeroing" is an inherent, necessary function to relate measured internal blood pressure to atmospheric pressure. It is performed repeatedly during a hospital stay wherein a patient is connected to a patient care monitor. Patients are commonly moved from one patient care monitor to another whenever transport from one location to another takes place. Each connection to a patient care monitor requires a repeat of the zeroing operation, and sometimes multiple zeroings are performed during a single patient care monitor experience for a variety of reasons (power failure, inadvertent disconnection, other electronic equipment failures).

One embodiment of the present invention has correction factors that are gauge factors, and those gauge factors for that sensor are necessary information for interpretation of the signals from the sensor. Therefore, some means of memory storage (EEPRO, EPROM, etc.) is routinely attached to a sensor, typically at the optical connector end (as opposed to the sensor end) on sensor incorporated into medical devices. Alternatively, the memory storage can be located on the BPM or in communication with the BPM. Sensor with the BPM also have gauge factors that can be stored in many means of internal memory.

While the invention is directed toward measuring blood pressure, the invention can also be used to measure cerebrospinal fluid pressure. Cerebrospinal fluid is the liquid in the human body that can be found around the brain and spinal cord. It is made by a group of cells which are called the choroid plexus which are located in the brain. The fluid is clear, and its functions include cushioning the brain and spinal cord, transporting supplies from the blood, and getting rid of waste produced by brain cells. The invention can also be utilized to determine venous pressure. Venous pressure is the pressure that correlates with the average blood pressure that is within the venous compartment. Furthermore, the invention can be utilized to measure bladder pressure and pulmonary artery pressure, etc. as well.

In FIG. 1, a perspective view of one embodiment of a blood pressure monitor system 100 that has its cover removed and pressure sensor exposed to atmospheric pressure is disclosed. Inside the BPM 105, there is a BPM sensor 101. The present invention is capable of being modified to work with any type of pressure sensor and is not limited by type, size, or method in which pressure is observed. Furthermore, in alternate embodiments, the BPM sensor 101 may not be attached to the BPM 105 and may be in communication with the BPM 105 through a wireless means. Alternatively, there may not be any blood pressure sensor at all. The atmospheric pressure observation may be sent to the BPM 105 by the patient care monitor.

The location of the BPM sensor 101 is not important to the present invention. The BPM sensor 101 in FIG. 1 is displayed inside the housing 106 of the BPM 105 affixed to a rear wall panel 102; however, it is not required to be located inside the BPM housing 106 of the BPM 105. In practice, the BPM sensor 101 could be situated outside the BPM housing 106 of the BPM 105 and coupled to it by a connector, cable and/or affixed to a part of the BPM housing 106 that is then coupled to a port that allows for the transfer of information from the BPM sensor 101 to the BPM 105. The displayed embodiment has the BPM sensor 101 be exposed to atmospheric pressure.

The BPM housing 106 of the BPM 105 may have, but does not require, a grate 103 situated on the rear wall of the rear wall panel 102. The grate 103 is illustrated to be generally symmetrical and possesses a set of small, round apertures 104 that allow for the passage of air from outside the BPM housing 106 to inside the BPM housing 106. This passage of air exposes the BPM sensor 101 to atmospheric pressure. The size and shape of the grate 103 and the apertures 104 is not specific. In alternate embodiments, the exposure of the BPM sensor 101 could be facilitated by a membrane or a vent or any acceptable means that allows for the passage of air through such that the BPM sensor 101 is exposed to atmospheric pressure. All that is required, however, is that the BPM 105 is not airtight such that the pressure inside the BPM housing 106 of the BPM 105 will freely equilibrate with atmospheric pressure. The BPM 105 and the BPM housing 106 can be configured to meet water ingress resistance standards in order to meet ISO 60601 regulatory standards and achieve FDA and CE Mark clearances. FIG. 1 further illustrates that the BPM housing 106 possesses a port 107 that possesses a connector apparatus 108 for coupling the BPM 105 to a medical device 209 such as one that is depicted in FIG. 2.

Figure 2:
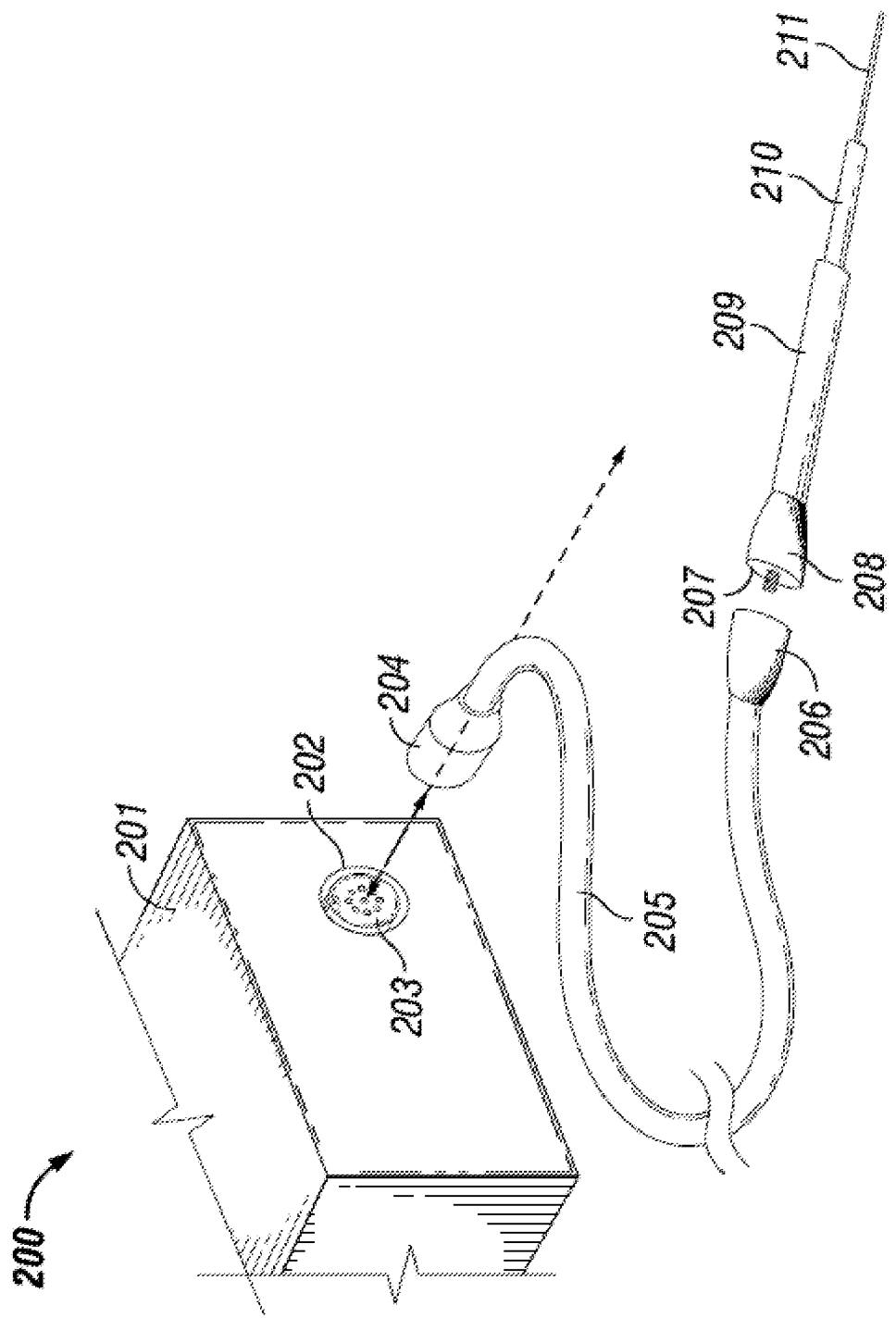
FIG. 2 is a perspective view of the present invention of one embodiment of the blood pressure monitoring system.

In FIG. 2, a perspective view of the present invention of one embodiment of the blood pressure monitoring system 200 is disclosed. The disclosed embodiment includes a medical device 210 for inserting into a patient that is coupled to a BPM 201 through a male connector 207 to a female cable connector 206, a cable 205, a male cable connector 204, and then to a female coupling device 203 that is inside of a port 202 which is affixed to the BPM 201. The cable 205 is preferable a fiber optic cable that utilizes the male end of a fiber optic connector 204 to be coupled with a female end of a fiber optic connector 203 contained in the port 202. However, the medical device 210 in the present invention can be adapted to be coupled to the BPM 201 through other types of cables which will probably be dictated by the type of sensor 211 used in the invention.

At the tip of the medical device 210 is the medical device sensor 211. The medical device is connected to catheter tubing 209 which is connected to a sensor connector 208 that utilizes a male connector 207 to interface with the cable through the female cable connector 206. While the medical device sensor 211 depicted in FIG. 2 is a Fabry-Perot pressure sensor which is a type of fiber optic sensor, the type of sensor is not required to be the aforementioned type of sensor. Generally, the invention can be configured to work with other types of sensors as well.

In the preferred embodiment of the present invention, the medical device sensor 211 is intended to be inserted into the vasculature of a patient such that the current blood pressure can be observed in situ. However, the invention can be configured to allow for the medical device sensor 211 to be situated outside the patient, including being level with the patient's heart, and connected to a patient through a catheter that has an end inserted inside the patient such that the analog sensor can observe the blood pressure inside the patent by being in fluidic contact with the vasculature of the patient.

Once the sheath 210 is inserted into the patient, the medical device sensor 211 is not required to be recalibrated in accordance with a current atmospheric pressure reading in order for an accurate blood pressure observation from the patient to be obtained. In the present embodiment, the BPM 201 initiates a zero function in order to obtain a current observation of atmospheric. The zero function is initiated when the BPM 201 in FIG. 2 detects that it has been coupled with a medical device 210. The zero function is performed by the BPM sensor by observing and recording the current atmospheric pressure. The observation of atmospheric pressure is utilized with the gauge factors that are specific to the BPM sensor, along with gauge factors that are specific to a medical device sensor that is coupled to the medical device, in order to derive a zero factor and retrieved from being stored in non-volatile memory. It is preferable, but not required, that the non-volatile memory be EPROM memory. Also, it is preferable, but not required, that a pre-existing zero factor be erased and replaced with the newly derived zero factor each time the zero function is initiated.

A Fabry-Perot sensor uses a continuous light signal to create an interference pattern ("interferometry") that varies as pressure varies, from which multiple samplings can create digital pressure values of discrete sampling frequencies.

The zero function in FIG. 2 can be initiated by a user by decoupling the medical device from the BPM 201, and then recoupling it.

Figure 3:
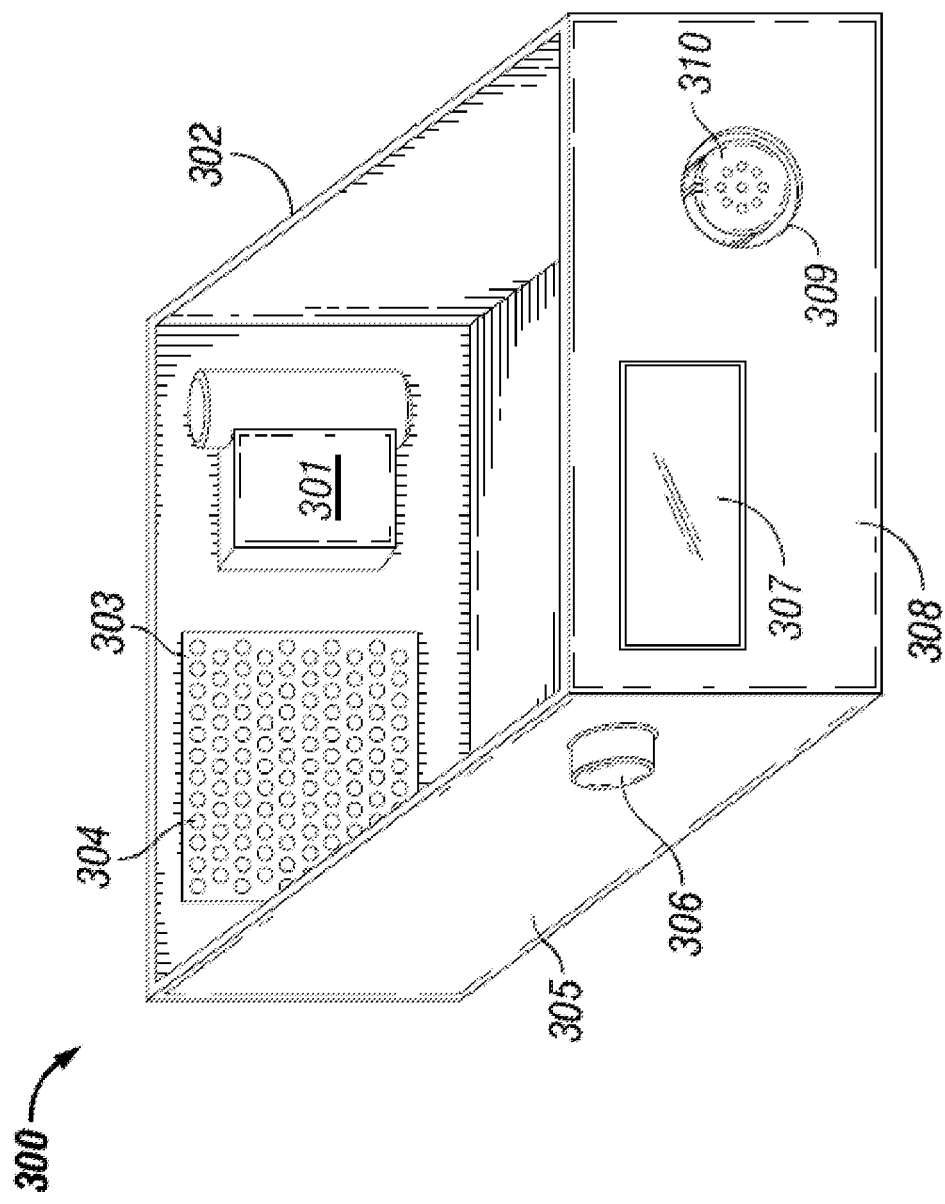
FIG. 3 is a perspective view of an alternate embodiment of a blood pressure monitor for the present invention.

In FIG. 3, a perspective view of an alternate embodiment of a blood pressure monitor system 300 and includes a display 307 on front panel 308. When a medical device is coupled to BPM 305 by utilizing the connector 310 that is located in port 309, the BPM 305 utilizes the BPM sensor 301 that is exposed to atmospheric pressure to take a pressure reading of the atmosphere. The BPM 305 may be exposed to the atmosphere by grate 303 which may have one or more apertures 304 that allow air to enter the BPM 305.

The atmospheric pressure reading is utilized with the correction factors that are specific to the medical device sensor and the correction factors that are specific to the BPM sensor 301 to derive the zero value. Note that the internal sensor in the BPM is continuously monitoring atmospheric pressure, and the readings of the internal sensor are matched at a given instant to the readings of the device sensor to "zero" the system. Then the zero value is stored in the non-volatile memory after any pre-existing zero value is erased. Once a blood pressure observation is received from the medical device, the blood observation is utilized with the zero value to produce the compensated pressure value.

In addition to the foregoing, the illustrated embodiment includes an initiation device 306 for allowing a user to initiate a zero function without having to decouple and recouple the medical device from the BPM 305—i.e., zero switch. By operating the initiation device 306, the user is dictating to the BPM 305 that the medical device sensor 301 that is exposed to atmospheric pressure take an atmospheric pressure reading even though the medical device has not been decoupled and then recoupled from the BPM 305. Once the atmospheric pressure reading has been taken, a new zero value is derived from the atmospheric pressure reading, the gauge factors that are specific to the BPM sensor 301 that is a part of the BPM 305, and the gauge factors that are specific to the medical device sensor. Then any pre-existing zero value is erased from the non-volatile memory and the new zero value is stored in its place.

Electronics, not shown, are located in the enclosure. The electronics would include the memory used to store the correction factors, and also a processor to adjust the measured pressure to a corrected pressure.

Figure 4:
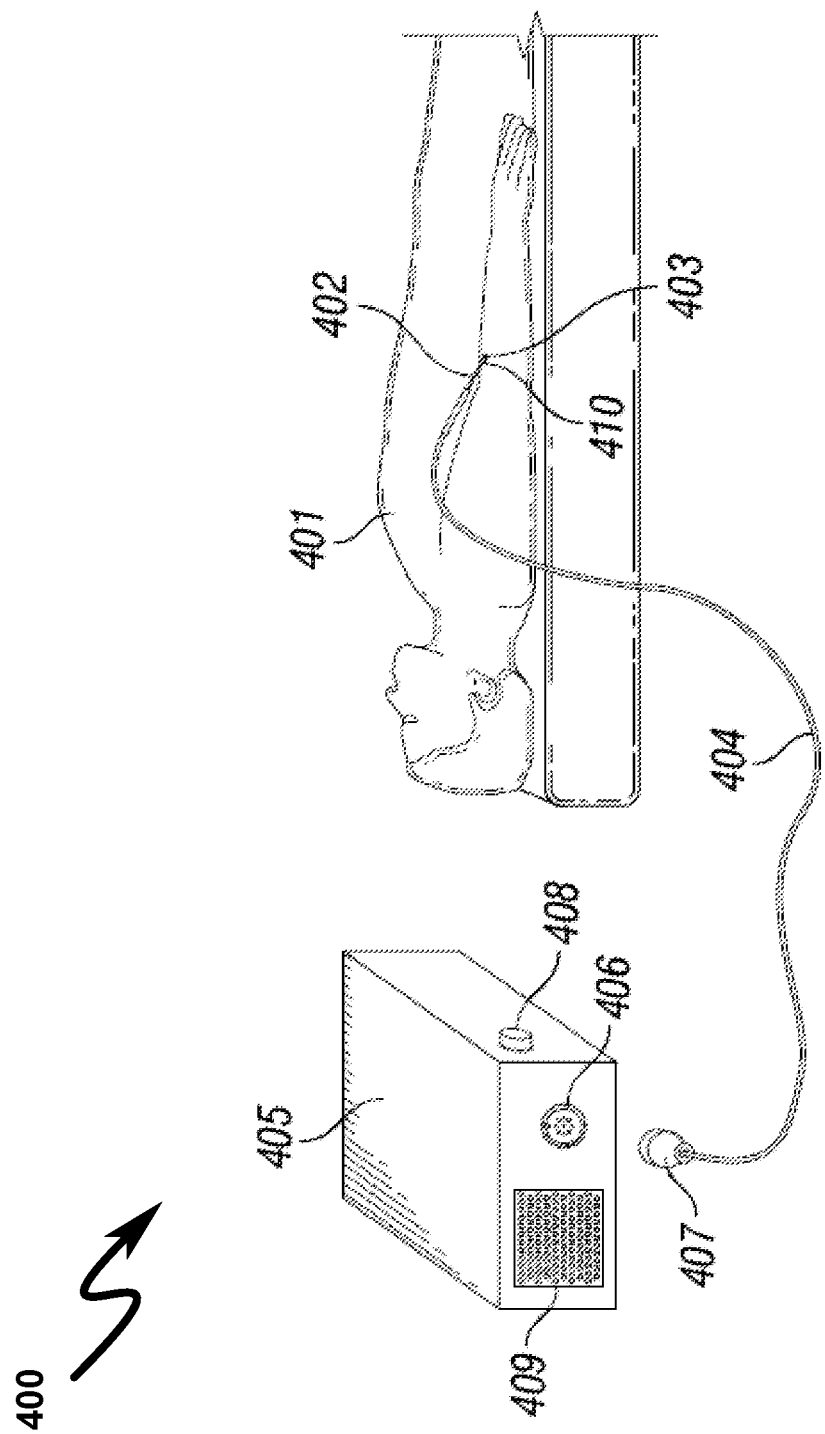
FIG. 4 is an environmental view of the blood pressure monitoring system utilized in a patient.

In FIG. 4, an environmental view of the blood pressure monitoring system 400 utilized in a patient is disclosed. The sheath has been inserted into a patient 401 at a point in the patient's body 403. The specific point 403 at which the sheath sensor is located in the patient 401 is going to depend on where the user intends to measure the patient's blood pressure. The sheath sensor 410 is inserted, along with the sheath 402, into the patient's body 401 at the desired point 403. Then the sheath 402 is coupled through a cable 404 with a connector 407 into the BPM 405 through a port 406. FIG. 4 further illustrates that the grate 409 may be located anywhere on the outside of the BPM 405, or may be normal ventilation pathways such as small spaces (i.e. not air-tight) around switches, etc., just as long as it allows for the BPM sensor inside to be exposed to atmospheric pressure. Also, included in FIG. 4 is the zero switch 408 which allows for the BPM 405 to initiate a zero function without decoupling and recoupling the sheath with the BPM 405.

Figure 5:
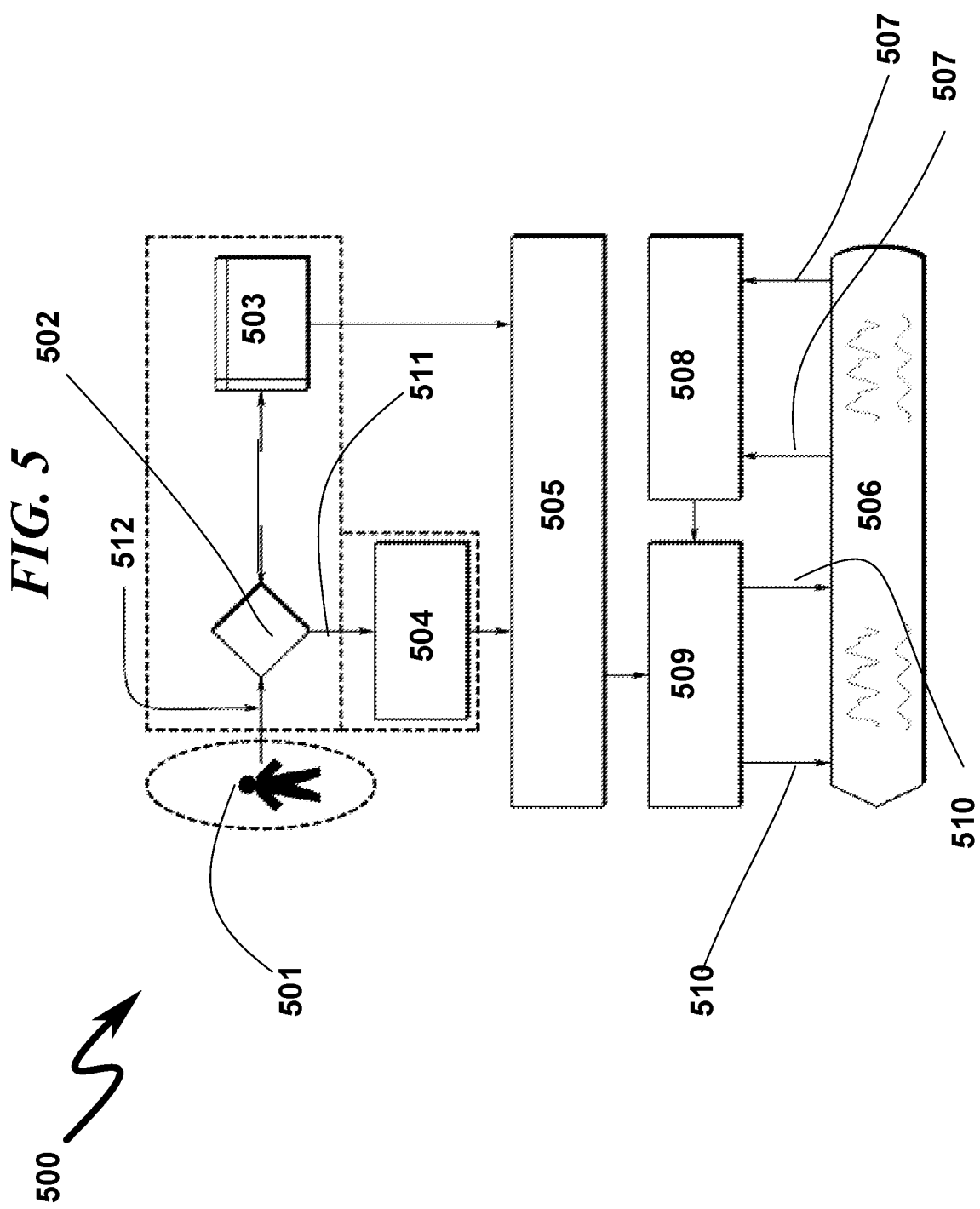
FIG. 5 is an illustration of a system block diagram of the transducer interface method system as applied to an analog patient status sensor monitored by a patient care monitor.

FIG. 5 provides a system block diagram of the transducer interface system 500. A patient 501 is shown with an analog patient status sensor 502 monitored by a patient care monitor 506. The transducer interface system 500 collects data associated with a patient 501 in a healthcare application context after a physical event 512 such as a recoupling of the analog sensor 502 to the patient 501 has occurred. The analog sensor 502 has associated correction factors 503 that describe a conversion from the analog values produced by the sensor 502 to a normalized set of standardized values. For example, a fiber optic pressure sensor might incorporate correction factors converting measured optical transit delays (or other measured physical data associated with the optical sensor) to absolute pressure values. In Fabry-Perot sensors, internal reflective surfaces on either side of a small cavity create a reflective pattern of different levels of returning light (interferometry), the pattern of which is used to calculate corresponding pressure values.

The analog sensor 502 creates an analog output 511 that is converted to digital signal by an A/D converter 504. This digital information, along with the correction factors 503, is presented to a microcontroller (MCU) 505 (or other computing device) for integration. In this step the raw analog sensor 502 information is compensated by the correction factors 503 to produce sensor data that may be interpolated, if necessary, to produce accurate sensor information that is accurate over a wide dynamic range of sensor inputs.

Within this general system context, in many preferred configurations, a patient care monitor 506 generates analog excitation signaling 507 that is used as a scaling reference for the Wheatstone Bridge emulator 508. The analog sensor A/D converter data and the correction factor data are combined to produce a Wheatstone Bridge sense output that is converted by a D/A converter 509 for combination with the excitation signaling data and subsequent presentation to the PCM 506 as an analog bridge sense signal 510. This analog bridge sense signal 510 represents a fully compensated and calibrated conversion of the analog sensor 502 output that is scaled in proper form for processing and display by the PCM 506. Further details of the transducer interface method system 500 can be found in the previous referenced U.S. Pat. No. 8,926,520.

Figure 6:
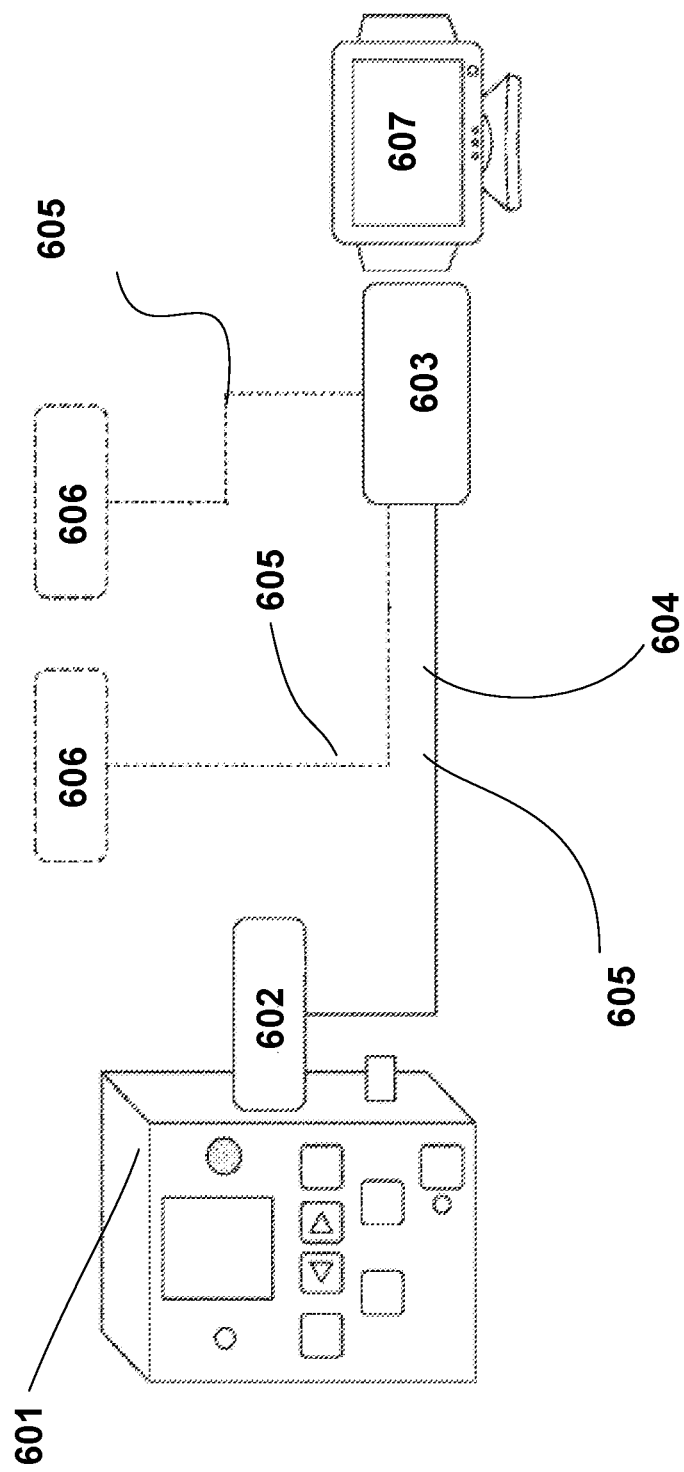
FIG. 6 illustrates a patient monitor cabling as applied to a blood pressure monitor system.

FIG. 6 illustrates a patient monitor cabling as applied to a blood pressure monitor system 600 is disclosed. The BPM 601 accepts standard analog invasive arterial blood pressure fluidic strain gauge connections from a wide variety of commercial patient monitors 607. These connections vary from one vendor to another, and multiple commercial connecting cable systems are employed in the industry. This disclosure incorporates a plurality of means of connection herein. The BPM 601 shall accept an excitation voltage from the patient care monitor 607 and deliver a correspondingly derived optically-sensed blood pressure signal 604 to the patient monitor 607 through an external connector 602 that is connected to the patient care monitor 607 via an adapter cable 605. The interface shall automatically detect the presence of a patient care monitor 607 and adjust its output based on the sensed excitation voltage applied. The interface will electrically emulate a common fluidic invasive arterial blood pressure transducer interface. This interface shall be continuously active at all times after the BPM 601 has successfully completed initialization. Additionally, a patent care monitor specific connector may connect between the adapter cable 605 and the BPM 601. The patent care monitor specific connector 603 allows for alternate BPMs 606 to be connected to send and receive signals through additional adapter cables 605 During periods when blood pressure sensor data is not being acquired from a fiber optic sensor, the signal output shall display a zero. Further details of the blood pressure monitor system 600 can be found in the previous referenced U.S. Pat. No. 8,926,520.

Figure 7:
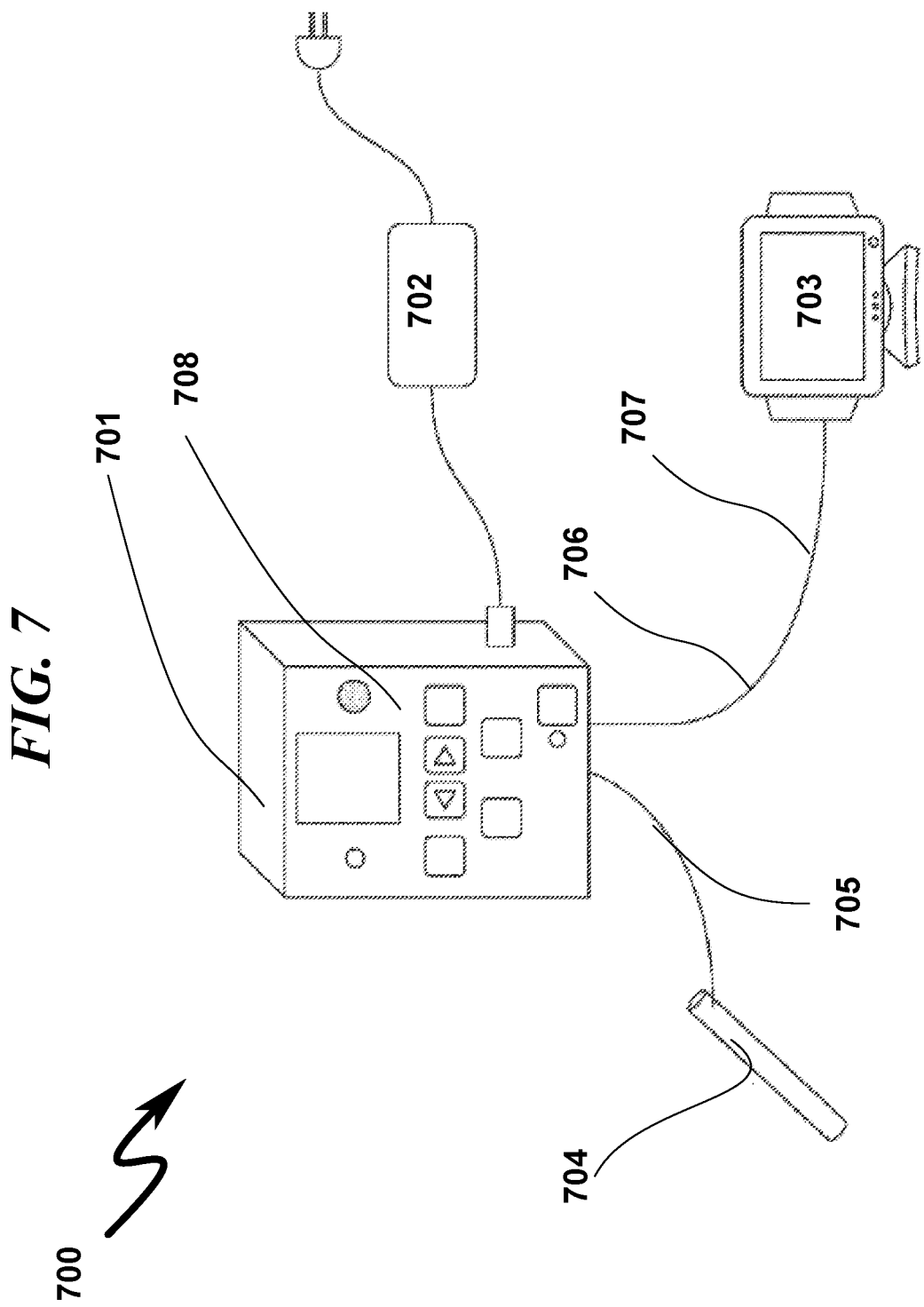
FIG. 7 is an illustration of a blood pressure monitor sensing sheath system as applied to a blood pressure monitor system.

FIG. 7 illustrates a blood pressure monitor sensing sheath system as applied to a blood pressure monitor system 700 is disclosed. The BPM 701 is connected to a patient care monitor 703. The patient care monitor 703 initiates the zero function by communicating to the BPM 701 through an adapter cable 706. In one embodiment, the medical device 704 takes an observation of atmospheric pressure prior to being inserted into a patient. An atmospheric pressure reading is communicated from the medical device 704 through a fiber optic cable 705 to the BPM 701. Then, the medical device 704 communicates the atmospheric pressure reading via the adapter cable 706 to the BPM 701 which calculates an adjusted atmospheric pressure. The BPM 701 calculates a zero value 707 and then communicates the zero value 707 to the medical device 704 to be stored in memory. The zero vale 707 can also be displayed on the user interface 708 coupled to the BPM 701. In addition, the BPM 701 is connected to a power module 703 to provide power to the BPM 701.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments but should be defined only in accordance with any claims and their equivalents issuing from this disclosure. Furthermore, the above advantages and features are provided in described embodiments but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

I claim:

1. A pressure monitoring system for use with at least one or more patient care monitors (PCM), the system comprising:
    a medical device in communication with a pressure monitor capable of obtaining an atmospheric pressure;
    a device sensor connected to the medical device and configured for insertion into a patient, wherein the device sensor measures a pressure within the patient;

at least one specific correction factor associated with the device sensor;

wherein the medical device facilitates the pressure monitor producing a zero function by observing an atmospheric pressure as adjusted by the correction factor(s) to create an adjusted atmospheric pressure, said zero function resulting in the pressure monitor setting the adjusted atmospheric pressure to a zero value in the device sensor;

a memory associated with the pressure sensor and storing the zero value and correction factor(s);

wherein, upon disconnection of the medical device from the pressure monitor and connection of the medical device to a second pressure monitor, the medical device facilitates the second pressure monitor determining if there is a stored zero value in the memory, and if there is not one then facilitates the second pressure monitor producing the zero function to provide a new zero value to the device sensor and store the new zero value in the memory; and a zero switch in communication with the medical device and configured for activating the zero function by the first or second pressure monitor.

2. The pressure monitor system of claim 1, wherein the observed atmospheric pressure is received from the PCM.

3. The pressure monitor system of claim 1, wherein the atmospheric pressure is calculated from an atmospheric pressure reading received from a pressure monitor sensor that is configured to communicate with the pressure monitor.

4. The pressure monitoring system of claim 1, wherein the observed atmospheric pressure is measured when stable over a predetermined period of time.

5. The pressure monitoring system of claim 1, wherein the measured pressure is measured when stable over a predetermined period of time.

6. The pressure monitoring system of claim 1, wherein the observed atmospheric pressure is averaged over a predetermined period of time.

7. The pressure monitoring system of claim 1, wherein the measured pressure is averaged over a predetermined period of time.

8. The pressure monitoring system of claim 1, wherein the measured pressure is selected from the group consisting of: a blood pressure; a cerebrospinal fluid pressure; a bladder pressure; a venous pressure; and a pulmonary artery pressure.

9. The pressure monitoring system of claim 1, wherein the memory is affixed to the medical device or to the pressure sensor.

10. The pressure monitoring system of claim 1, wherein the memory is a non-volatile memory.

11. The pressure monitoring system of claim 10, wherein the non-volatile memory is an EPROM memory or an EEPROM memory.

12. The pressure monitoring system of claim 1, wherein the device sensor comprises a fiber optic pressure sensor.

13. The pressure monitoring system of claim 1, wherein the medical device is selected from the group consisting of: a sheath, a catheter, a guidewire, and a needle.

14. The pressure monitoring system of claim 1, wherein the medical device is coupled to the pressure monitor by a fiber optic cable.

15. A pressure monitoring method, comprising:
obtaining an atmospheric pressure with a pressure monitor;

measuring pressure within a patient with a device sensor configured for insertion into the patient;

storing, in a memory, at least one specific correction factor associated with the device sensor;

producing, with the pressure monitor, a zero function by creating an adjusted atmospheric pressure from the obtained atmospheric pressure as adjusted by the correction factor(s);

setting, with the pressure monitor, the adjusted atmospheric pressure to a zero value in the device sensor;

upon interruption of communication from the pressure sensor to the pressure monitor and reestablishment of communication from the pressure sensor to the pressure monitor or to a second pressure monitor, generating, from the pressure monitor or second pressure monitor, an indication that a new zero function needs to be produced; and in response to the generating of the indication, producing, with the pressure monitor or second pressure monitor, the new zero function to provide a new zero value to the device sensor and store the new zero value in a memory.

16. The method of claim 15, wherein obtaining the atmospheric pressure comprises receiving the atmospheric pressure from a patient care monitor associated with the pressure monitor or the second pressure monitor.

17. The method of claim 15, wherein the obtaining the atmospheric pressure comprises calculating the atmospheric pressure from an atmospheric pressure reading received from a pressure monitor sensor that is configured to communicate with the pressure monitor.

18. The method of claim 15, wherein the obtaining the atmospheric pressure comprises measuring the atmospheric pressure when stable over a predetermined period of time.

19. The method of claim 15, wherein the obtaining the atmospheric pressure comprises averaging atmospheric pressure over a predetermined period of time.

20. The method of claim 15, wherein the measuring pressure comprises measuring pressure selected from the group consisting of: a blood pressure; a cerebrospinal fluid pressure; a bladder pressure; a venous pressure; and a pulmonary artery pressure.

* * * * *